United States Patent [19]

Duvall et al.

[11] Patent Number: 4,942,039

[45] Date of Patent: Jul. 17, 1990

[54] EFFERVESCENT ANALGESIC ANTACID COMPOSITION HAVING REDUCED SODIUM CONTENT

[75] Inventors: Ronald N. Duvall; Gerald Gold, both of Elkhart, Ind.

[73] Assignee: Miles Inc., Elkhart, Ind.

[21] Appl. No.: 401,064

[22] Filed: Sep. 5, 1989

Related U.S. Application Data

[63] Continuation-in-part of Ser. No. 349,113, May 9, 1989, abandoned, which is a continuation-in-part of Ser. No. 296,537, Jan. 12, 1989, abandoned.

[51] Int. Cl.$^5$ ................................................. A61K 9/46
[52] U.S. Cl. .................................... 424/466; 424/464; 424/465
[58] Field of Search .................. 424/466, 465, 464; 514/960

[56] References Cited

U.S. PATENT DOCUMENTS

| | | | |
|---|---|---|---|
| 2,297,599 | 9/1942 | Wilen | 424/466 |
| 2,854,377 | 9/1958 | Elias | 167/58 |
| 2,953,459 | 9/1960 | Diller | 99/78 |
| 2,985,562 | 5/1961 | Millard et al. | 167/57 |
| 3,102,075 | 8/1963 | Millard | 167/57 |
| 3,105,792 | 10/1963 | White | 167/57 |
| 3,136,692 | 6/1964 | Bandelin | 167/57 |
| 3,243,377 | 3/1966 | Stolar et al. | 252/95 |
| 3,495,001 | 2/1970 | Leonards | 424/44 |
| 3,518,343 | 6/1970 | Welsh et al. | 424/44 |
| 3,903,255 | 9/1975 | Gusman et al. | 424/44 |
| 3,961,041 | 6/1976 | Nishimura et al. | 424/466 |
| 4,036,728 | 7/1977 | Theeuwes | 424/466 X |
| 4,093,710 | 6/1978 | Sass et al. | 424/44 |
| 4,265,874 | 5/1981 | Bonsen et al. | 424/466 X |
| 4,303,548 | 12/1981 | Shimazaki et al. | 424/466 X |
| 4,704,269 | 11/1987 | Korab | 424/44 |

FOREIGN PATENT DOCUMENTS 1505738 3/1978 United Kingdom .............. 424/466

OTHER PUBLICATIONS

Mohrle, Raymond, 1989, Pharmaceutical Dosage Form, vol. 1, pp. 225–258.

*Primary Examiner*—Thurman K. Page
*Attorney, Agent, or Firm*—L. E. Davidson

[57] ABSTRACT

An effervescent analgesic antacid composition having reduced sodium content is produced from a mixture of an analgesic, such as acetylsalicylic acid, acetaminophen, ketoprofen or a mixture thereof, citric acid, sodium bicarbonate, calcium carbonate, potassium bicarbonate, and minor amounts of flavors and sweeteners.

9 Claims, No Drawings

EFFERVESCENT ANALGESIC ANTACID COMPOSITION HAVING REDUCED SODIUM CONTENT

This is a continuation-in-part application of U.S. patent application Ser. No. 07/349,113, filed on May 9, 1989, now abandoned which is a continuation-in-part appplication of U.S. patent application Ser. No. 07/296,537, filed on Jan. 12, 1989, now abandoned.

BACKGROUND OF THE INVENTION AND PRIOR ART

Effervescent analgesic antacid compositions containing acetylsalicylic acid as the analgesic component and citric acid and sodium bicarbonate as the principal ingredients of an effervescent couple have been known for many years. One of the disadvantages of these compositions is the elevated sodium content which renders them unsuitable for individuals who should reduce their sodium intake. While efforts have been made in the prior art to produce such compositions having reduced sodium content by including calcium carbonate and potassium bicarbonate, for example, the resulting products form solutions that have an unpleasant taste. When acetaminophen, which has an unpleasant taste itself, is used to replace all or a part of the acetylsalicylic acid as the analgesic component, the resulting product has been generally unacceptable from a taste standpoint.

Another problem with prior art effervescent analgesic antacid compositions having reduced sodium content is that they do not completely dissolve. They form a cloudy or milky solution with a scum of undissolved particles floating on the surface of the liquid.

Ketoprofen is another analgesic compound that is suitable for use in an effervescent analgesic antacid composition.

There is thus a need for an effervescent analgesic antacid composition containing acetylsalicylic acid, acetaminophen, ketoprofen or mixtures thereof as the analgesic component and reduced sodium content in the effervescent couple/antacid component which forms a solution that is pleasant tasting. There is also a need for such composition that will substantially completely dissolve in water to form a clear solution with no scum on the liquid surface.

U.S. Pat. No. 3,495,001 discloses a sodium-free effervescent analgesic composition. U.S. Pat. Nos. 2,854,377; 2,953,459; 2,985,562; 3,102,075; 3,105,792; 3,136,692; 3,243,377; 3,518,343; 3,903,255; and 4,093,710 disclose various effervescent compositions containing various amounts and combinations of glycine, surfactants such as dioctyl sodium sulfosuccinate, fumaric acid and polyvinyl pyrrolidone. I. R. Mohrle, "Pharmaceutical Dosage Forms: Tablets", Vol. 1, Marcel Dekker, Inc., New York, NY, pp. 225-258 (1980) provides a full description of various effervescent tablet formulations and their ingredients. U.S. Pat. No. 4,704,269 discloses an effervescent analgesic antacid composition having reduced sodium content wherein the antacid and a food grade acid reactive therewith to form the effervescent couple are in the form of an agglomerate held together by a water soluble food grade binder.

None of the above prior art disclosures specifically disclose or suggest the novel compositions of the present invention.

SUMMARY OF THE INVENTION

According to this invention, there is provided an effervescent analgesic antacid composition having a reduced sodium content which is capable of being dissolved in water to form a pleasant tasting solution which comprises a mixture of 0.2-16% acetylsalicylic acid, acetaminophen, ketoprofen or mixtures thereof, 26-40% citric acid, 13-21% sodium bicarbonate, 7-12% calcium carbonate, 8-14% potassium bicarbonate, 0-14% glycine, 0.8-1.5% flavors and sweeteners, 0-31% tableting aids other than lubricants, and 0-6% tablet lubricant other than acetylsalicylic acid, said percents being weight percent based on the total weight of the composition.

DESCRIPTION OF THE INVENTION

Acetylsalicylic acid, acetaminophen, ketoprofen or a mixture thereof provides the analgesic component of this composition. The antacid component is provided primarily by a mixture of sodium bicarbonate, calcium carbonate, and potassium bicarbonate. The effervescent couple is provided by citric acid reacting with the carbonates and bicarbonates of the antacid component.

When acetylsalicylic acid, acetaminophen or mixture thereof is the analgesic, it is employed in an amount to produce a dose containing 325-500 mg. of the analgesic. When ketoprofen is the analgesic, it is employed in an amount to produce a dose containing 6.25-50 mg. of the analgesic. The calcium carbonate should be employed in an amount so as to provide a total daily dosage not exceeding 8 g. The calcium carbonate is preferably employed in the spray-dried form described in U.S. Pat. No. 4,650,669. The potassium bicarbonate is employed in an amount not to exceed a total daily dose of 2.5 g. If desired, glycine may be employed to achieve a desired level of acid neutralizing capacity. The resulting composition when dissolved in water produces a pH of 4-6.

The taste of the product after it is dissolved in water can be improved by including in the composition minor amounts of flavors, such as lemon, grapefruit and orange flavors, as well as sweeteners, such as aspartame and calcium or sodium saccharin. The aspartame may be used in the form of granules containing lactose and a nonionic surfactant as described in U.S. Pat. No. 4,783,331.

This composition can be used in a powder-granulated form or it can be used in the form of compressed tablets. In the production of tablets a lubricant is necessary for the tablet dies. When a significant amount of acetylsalicylic acid is present in the formulation, it will function as a lubricant. When acetylsalicylic acid is not used or is present in minor amounts, it is desirable for fumaric acid to be used as a lubricant. It is understood, however, that other well-known tablet lubricants, such as adipic acid and sodium benzoate, can also be used. It is also preferable to include tableting aids other than lubricants, such as inert fillers or binders. Examples of such fillers or binders are sorbitol, lactose, mannitol, fructose, sucrose, a co-crystallized mixture of 97% sucrose and 3% modified dextrins or hydroxypropylmethylcellulose. It is preferred that the major component of the tableting aids other than lubricants be sorbitol.

In order to have a substantially completely dissolved product with no scum floating on the liquid surface, it is preferable to include in the composition minor amounts of polyvinyl pyrrolidone, organopolysiloxane (such as dimethyl polysiloxane), and dioctyl sodium sulfosuccinate surfactant.

The composition of the present invention contains 0.2-16% of an analgesic selected from the class consisting of acetylsalicylic acid, acetaminophen, ketoprofen and mixtures thereof, 26-40% citric acid, 13-21% sodium bicarbonate, 7-12% calcium carbonate, 8-14% potassium bicarbonate, 0-14% glycine, 0.8-1.5% flavors and sweeteners, 0-31% tableting aids other than lubricants, and 0-6% tablet lubricant other than acetylsalicylic acid. Preferably, the composition contains 0.2-16% acetylsalicylic acid, acetaminophen, ketoprofen or mixtures thereof, 26-30% citric acid, 13-16% sodium bicarbonate, 7-9% calcium carbonate, 8-10% potassium bicarbonate, 0-13% glycine, 0.8-1.5% flavors and sweeteners, 11-26% tableting aids other than lubricants, 2-6% fumaric acid, about 0.03-0.04% polyvinyl pyrrolidone, about 0.01-0.02% organopolysiloxane, and about 0.001-0.002% dioctyl sodium sulfosuccinate. All of the above percents are weight percent based on the total weight of the composition.

The final form of the composition is produced by dry blending all the ingredients. Final tablet forms are produced by feeding the above mixture to a tablet press in a manner known to those skilled in the art.

The following example describes production of tablets of one form of the preferred composition.

EXAMPLE 1

A 5100 g. quantity of granulated acetaminophen (containing 95.6 weight percent acetaminophen, 3.8 weight percent citric acid, and 0.6 weight percent hydroxypropylmethylcellulose) was passed through a Fitzpatrick Comminutor Model D operating at 4500 rpm. A 6000 g. quantity of glycine and a 4500 g. quantity of potassium bicarbonate were separately dried at 130° F. (54.44° C.) for 16 hr. A mixture of 5955.9 g. sorbitol, 15 g. polyvinyl pyrrolidone, 7.5 g. of dimethyl polysiloxane, 0.75 g. dioctyl sodium sulfosuccinate (in the form of a mixture containing 85% dioctyl sodium sulfosuccinate and 15% sodium benzoate), 4500 g. above-dried potassium bicarbonate and 1425 g. fumaric acid was rough-mixed by passing it through a Fitzpatrick Comminutor Model D at 2500 rpm. This latter mixture was then final mixed with the above acetaminophen and glycine along with 250.5 g. of a mixture of lemon, grapefruit and orange flavors, 550.35 g. of aspartame granules (of the type described in U.S. Pat. No. 4,783,331 containing 78.61% lactose, 0.95% nonionic surfactant and 20.44% aspartame), 45 g. calcium saccharin, 4500 g. spray-dried calcium carbonate (containing 83% calcium carbonate, 9.95% lactose and 7.05% maltodextrin of the type described in U.S. Pat. No. 4,650,669), 13275 g. anhydrous citric acid and 7125 g. sodium bicarbonate that had been heat-treated as described in U.S. Pat. No. 3,105,792 in a 3 cu. ft. V-Blender for 15 minutes. The final mixture was then fed to a tablet press to produce tablets each containing 325 mg. acetaminophen and having a composition of:

| Weight % | Ingredient |
| --- | --- |
| 10.00 | Acetaminophen |
| 27.63 | Citric Acid |
| 14.62 | Sodium Bicarbonate |
| 7.66 | Calcium Carbonate |
| 9.23 | Potassium Bicarbonate |
| 12.31 | Glycine |
| 0.84 | Flavors and Sweeteners |
| 14.75 | Sorbitol and Other Tableting Aids Other than Lubricants |
| 2.92 | Fumaric Acid |
| 0.03 | Polyvinyl Pyrrolidone |
| 0.02 | Dimethyl Polysiloxane |
| 0.002 | Dioctyl Sodium Sulfosuccinate |
| 100.012 | |

When one or two of the above-produced tablets were placed in a glass containing about 4 oz. (118 ml.) water, there was significant effervescence while the tablet(s) dissolved resulting in a substantially clear solution with no scum on the liquid surface. This solution had a pleasant taste with no undesirable after-taste.

The following examples describe production of other forms of the composition of this invention.

EXAMPLE 2

The formulation of Example 1 is modified to increase the tablet content of acetaminophen to 500 mg. The sorbitol content is reduced to compensate for this keeping all the other ingredients the same. The tablet product has the composition of:

| Weight % | Ingredient |
| --- | --- |
| 15.00 | Acetaminophen |
| 27.15 | Citric Acid |
| 14.25 | Sodium Bicarbonate |
| 7.47 | Calcium Carbonate |
| 9.00 | Potassium Bicarbonate |
| 12.00 | Glycine |
| 0.82 | Flavors and Sweeteners |
| 11.41 | Tableting Aids Other than Lubricants |
| 2.85 | Fumaric Acid |
| 0.03 | Polyvinyl Pyrrolidone |
| 0.02 | Dimethyl Polysiloxane |
| 0.002 | Dioctyl Sodium Sulfosuccinate |
| 100.002 | |

EXAMPLE 3

The formulation of Example 1 is used with the direct substitution of acetylsalicylic acid for acetaminophen. The fumaric acid is deleted since the acetylsalicylic acid also functions as a lubricant. The sorbitol content is adjusted to maintain a constant tablet weight. The tablets containing 325 mg. acetylsalicylic acid have the composition of:

| Weight % | Ingredient |
| --- | --- |
| 10.00 | Acetylsalicylic Acid |
| 27.23 | Citric Acid |
| 14.62 | Sodium Bicarbonate |
| 7.66 | Calcium Carbonate |
| 9.23 | Potassium Bicarbonate |
| 12.31 | Glycine |
| 0.84 | Flavors and Sweeteners |
| 18.07 | Tableting Aids Other Than Lubricants |
| 0.03 | Polyvinyl Pyrrolidone |
| 0.02 | Dimethyl Polysiloxane |
| 0.002 | Dioctyl Sodium Sulfosuccinate |
| 100.012 | |

EXAMPLE 4

The formulation of Example 3 is modified to increase the tablet content of acetylsalicylic acid to 500 mg. The sorbitol content is reduced to compensate for this keeping all the other ingredients the same. The tablet product has the composition of:

| Weight % | Ingredient |
|---|---|
| 15.00 | Acetylsalicylic Acid |
| 26.56 | Citric Acid |
| 14.25 | Sodium Bicarbonate |
| 7.47 | Calcium Carbonate |
| 9.00 | Potassium Bicarbonate |
| 12.00 | Glycine |
| 0.82 | Flavors and Sweeteners |
| 14.86 | Tableting Aids Other Than Lubricants |
| 0.03 | Polyvinyl Pyrrolidone |
| 0.02 | Dimethyl Polysiloxane |
| 0.002 | Dioctyl Sodium Sulfosuccinate |
| 100.012 | |

EXAMPLE 5

The formulation of Example 1 is modified to produce a tablet containing 162.5 mg. acetaminophen and 162.5 mg. acetylsalicylic acid. The sorbitol content is adjusted to compensate for this and the fumaric acid is reduced to an amount necessary for adequate lubrication. The tablet produced has the composition of:

| Weight % | Ingredient |
|---|---|
| 5.00 | Acetaminophen |
| 5.00 | Acetylsalicylic Acid |
| 27.43 | Citric Acid |
| 14.62 | Sodium Bicarbonate |
| 7.66 | Calcium Carbonate |
| 9.23 | Potassium Bicarbonate |
| 12.31 | Glycine |
| 0.84 | Flavors and Sweeteners |
| 16.33 | Tableting Aids Other Than Lubricants |
| 1.54 | Fumaric Acid |
| 0.03 | Polyvinyl Pyrrolidone |
| 0.02 | Dimethyl Polysiloxane |
| 0.002 | Dioctyl Sodium Sulfosuccinate |
| 100.012 | |

EXAMPLE 6

The formulation of Example 5 is modified to increase the tablet content of acetaminophen and acetylsalicylic acid each to 250 mg. The sorbitol content is reduced to compensate and the fumaric acid is deleted. The tablet product has the composition of:

| Weight % | Ingredient |
|---|---|
| 7.69 | Acetaminophen |
| 7.69 | Acetylsalicylic Acid |
| 27.54 | Citric Acid |
| 14.62 | Sodium Bicarbonate |
| 7.66 | Calcium Carbonate |
| 9.23 | Potassium Bicarbonate |
| 12.31 | Glycine |
| 0.84 | Flavors and Sweeteners |
| 12.38 | Tableting Aids Other Than Lubricants |
| 0.03 | Polyvinyl Pyrrolidone |
| 0.02 | Dimethyl Polysiloxane |
| 0.002 | Dioctyl Sodium Sulfosuccinate |
| 100.012 | |

EXAMPLE 7

The formulation of Example 3 is modified to remove the glycine and the tableting aids. The product has the composition of:

| Weight % | Ingredient |
|---|---|
| 14.36 | Acetylsalicylic Acid |
| 39.11 | Citric Acid |
| 20.99 | Sodium Bicarbonate |
| 11.00 | Calcium Carbonate |
| 13.26 | Potassium Bicarbonate |
| 1.20 | Flavors and Sweeteners |
| 0.04 | Polyvinyl Pyrrolidone |
| 0.02 | Dimethyl Polysiloxane |
| 0.002 | Dioctyl Sodium Sulfosuccinate |
| 99.982 | |

EXAMPLE 8

The formulation of Example 3 is modified to remove the glycine but retain tableting aids. The overall tablet weight is the same. The product has the composition of:

| Weight % | Ingredient |
|---|---|
| 10.0 | Acetylsalicylic Acid |
| 27.23 | Citric Acid |
| 14.62 | Sodium Bicarbonate |
| 7.66 | Calcium Carbonate |
| 9.23 | Potassium Bicarbonate |
| 0.84 | Flavors and Sweeteners |
| 30.38 | Tableting Aids Other Than Lubricants |
| 0.03 | Polyvinyl Pyrrolidone |
| 0.02 | Dimethyl Polysiloxane |
| 0.002 | Dioctyl Sodium Sulfosuccinate |
| 100.012 | |

The following example describes production of tablets of another form of the preferred composition.

EXAMPLE 9

A 102 kg. quantity of granulated acetaminophen (containing 95.6 weight percent acetaminophen, 3.8 weight percent citric acid, and 0.6 weight percent hydroxypropylmethyl cellulose) was passed through a Fitzpatrick Comminutor Model D at 4500 rpm. A 64.67 kg. quantity of glycine was dried at 130° F. (54.44° C.) for 16 hr. Potassium bicarbonate granules were prepared by mixing 90 kg. of potassium bicarbonate with 9.9 kg. of 40 weight percent aqueous sodium citrate solution in a Littleford-Lodige Mixer and then drying the resulting granules at 180° F. (82.22° C.) for at least 22 hr. Such granules were then passed through a Fluid Aire Mill operating at 1500 rpm. A premix of 0.3 kg. polyvinyl pyrrolidone, 0.15 kg. dimethyl polysiloxane and 0.015 kg. of dioctyl sodium sulfosuccinate (in the form of a mixture containing 85 weight percent dioctyl sodium sulfosuccinate and 15 weight percent sodium benzoate) was prepared by passing such materials through a Fitzpatrick Comminutor Model D at 4700 rpm. A 40.5 kg. quantity of fumaric acid was passed through a Fitzpatrick Comminutor Model D at 2500 rpm. All of the above materials along with 150 kg. sorbitol, 5.01 kg. of a mixture of lemon, grapefruit and orange flavors, 0.9 kg. calcium saccharin, 11.007 kg. aspartame granules (containing 20.44 weight percent aspartame as described in Example 1), 101.1 kg. spray-dried calcium carbonate (containing 83 weight percent calcium carbonate as described in Example 1), 266.1 kg. anhydrous citric acid, and 139.5 kg. sodium bicarbonate that had been heat-treated as described in U.S. Pat. No. 3,105,792 were mixed in an Englesmann Mixer at 20 rpm for 14 minutes. The final mixture was then fed to a tablet press to produce tablets each containing 325 mg. acetaminophen and having a composition of:

| Weight % | Ingredient |
| --- | --- |
| 10.00 | Acetaminophen |
| 27.69 | Citric Acid |
| 14.31 | Sodium Bicarbonate |
| 8.62 | Calcium Carbonate |
| 9.23 | Potassium Bicarbonate |
| 6.63 | Glycine |
| 0.84 | Flavors and Sweeteners |
| 18.48 | Sorbitol and Other Tableting Aids |
| 4.15 | Fumaric Acid |
| 0.03 | Polyvinyl Pyrrolidone |
| 0.02 | Dimethyl Polysiloxane |
| 0.002 | Dioctyl Sodium Sulfosuccinate |
| 100.002 | |

When the above tablet product was placed in water, there was significant effervescence while the tablet dissolved resulting in a substantially clear solution with no scum on the liquid surface. This solution had a pleasant taste with no undesirable after-taste.

EXAMPLE 10

The formulation of Example 9 is modified to remove the glycine but retain tableting aids. The overall dose weight is the same. The product has the composition of:

| Weight % | Ingredient |
| --- | --- |
| 10.00 | Acetaminophen |
| 27.69 | Citric Acid |
| 14.31 | Sodium Bicarbonate |
| 8.62 | Calcium Carbonate |
| 9.23 | Potassium Bicarbonate |
| 0.84 | Flavors and Sweeteners |
| 25.11 | Tableting Aids |
| 4.15 | Fumaric Acid |
| 0.03 | Polyvinyl Pyrrolidone |
| 0.02 | Dimethyl Polysiloxane |
| 0.002 | Dioctyl Sodium Sulfosuccinate |
| 100.002 | |

EXAMPLE 11

The formulation of Example 9 was modified to increase the tablet content of acetaminophen to 500 mg. The sweetener content was increased and the glycine and tableting aids other than lubricants were adjusted appropriately. The other ingredients remained the same. The tablet product had the composition of:

| Weight % | Ingredient |
| --- | --- |
| 14.75 | Acetaminophen |
| 26.70 | Citric Acid |
| 13.72 | Sodium Bicarbonate |
| 8.26 | Calcium Carbonate |

-continued

| Weight % | Ingredient |
| --- | --- |
| 8.85 | Potassium Bicarbonate |
| 3.93 | Glycine |
| 1.49 | Flavors and Sweeteners |
| 18.41 | Sorbitol and Other Tableting Aids |
| 3.84 | Fumaric Acid |
| 0.03 | Polyvinyl Pyrrolidone |
| 0.01 | Dimethyl Polysiloxane |
| 0.001 | Dioctyl Sodium Sulfosuccinate |
| 99.991 | |

EXAMPLE 12

The formulation of Example 1 is modified to substitute 6.25 mg. ketoprofen for 325 mg. acetaminophen. The other ingredients remain the same. The tablet product has the composition of:

| Weight % | Ingredient |
| --- | --- |
| 0.21 | Ketoprofen |
| 30.35 | Citric Acid |
| 16.29 | Sodium Bicarbonate |
| 8.54 | Calcium Carbonate |
| 10.29 | Potassium Bicarbonate |
| 13.72 | Glycine |
| 0.93 | Flavors and Sweeteners |
| 16.36 | Sorbitol and Other Tableting Aids |
| 3.26 | Fumaric Acid |
| 0.03 | Polyvinyl Pyrrolidone |
| 0.02 | Dimethyl Polysiloxane |
| 0.002 | Dioctyl Sodium Sulfosuccinate |
| 100.002 | |

EXAMPLE 13

The formulation of Example 12 is modified to increase the ketotprofen content to 50 mg. The other ingredients remain the same.

What is claimed is:

1. An effervescent analgesic antacid composition having a reduced sodium content which is capable of being dissolved in water to form a pleasant tasting solution which comprises a mixture of 0.2–16% of an analgesic selected from the class consisting of acetylsalicylic acid, acetaminophen, ketoprofen and mixtures thereof, 26–40% citric acid, 13–21% sodium bicarbonate, 7–12% calcium carbonate, 8–14% potassium bicarbonate, 0–14% glycine, 0.8–1.5% flavors and sweeteners, 0–31% tableting aids other than lubricants, and 0–6% tablet lubricant other than acetylsalicylic acid, said percents being weight percent based on the total weight of the composition.

2. A composition of claim 1 suitable for forming tablets which are capable of being dissolved in water to form a pleasant tasting solution which contains 11–31% tableting aids other than lubricants and 1–6% tablet lubricant other than acetylsalicylic acid.

3. A composition of claim 2 which also contains about 0.03–0.04% polyvinyl pyrrolidone, about 0.01–0.02% organopolysiloxane and about 0.001–0.002% dioctyl sodium sulfosuccinate.

4. A composition of claim 2 wherein the major component of the tableting aids is sorbitol and the tablet lubricant is fumaric acid.

5. An effervescent analgesic antacid composition having a reduced sodium content suitable for forming tablets which are capable of being substantially completely dissolved in water forming a pleasant tasting solution which consists essentially of a mixture of 0.2–16% of an analgesic selected from the class consisting of acetylsalicylic acid, acetaminophen, ketoprofen and mixtures thereof, 26–30% citric acid, 13–16% sodium bicarbonate, 7–9% calcium carbonate, 8–10% potassium bicarbonate, 0–13% glycine, 0.8–1.5% flavors and sweeteners, 11–26% tableting aids other than lubricants, 2–6% fumaric acid, about 0.03–0.04% polyvinyl pyrrolidone, about 0.01–0.002% organopolysiloxane, and about 0.001–0.002% dioctyl sodium sulfosuccinate, said percents being weight percent based on the total weight of the composition.

6. A composition of claim 5 wherein the analgesic is acetaminophen.

7. A composition of claim 5 wherein the analgesic is acetylsalicylic acid.

8. A composition of claim 5 wherein the analgesic is a mixture of acetaminophen and acetylsalicylic acid.

9. A composition of claim 5 wherein the analgesic is ketoprofen.

* * * * *